United States Patent

Derible et al.

[11] 3,947,578
[45] Mar. 30, 1976

[54] OMEGA-[4-(3″-INDOLYL)-PIPERIDINO]-ALKYL-ARYLKETONES AS NEVROLEPTICS

[75] Inventors: Pierre Henri Derible, Le Perreux; Jean-Paul Lavaux, Paris, both of France

[73] Assignee: Roussel Uclaf, Paris, France

[22] Filed: Sept. 18, 1974

[21] Appl. No.: 506,964

Related U.S. Application Data

[62] Division of Ser. No. 380,407, July 18, 1973, Pat. No. 3,850,938.

[30] Foreign Application Priority Data

July 29, 1972 France .............. 72.27263

[52] U.S. Cl. .............. 424/267
[51] Int. Cl.² .............. A61K 31/445
[58] Field of Search .............. 424/267

[56] References Cited
UNITED STATES PATENTS

| | | | |
|---|---|---|---|
| 3,287,461 | 11/1966 | Gray | 260/296 |
| 3,361,759 | 1/1968 | Anthony et al. | 260/326.14 |
| 3,445,472 | 5/1969 | Archibald | 260/293.4 |

*Primary Examiner*—Stanley J. Friedman
*Attorney, Agent, or Firm*—Hammond & Littell

[57] ABSTRACT

Novel [4′-(3″-indolyl)-piperidino]-alkyl-arylketones of the formula

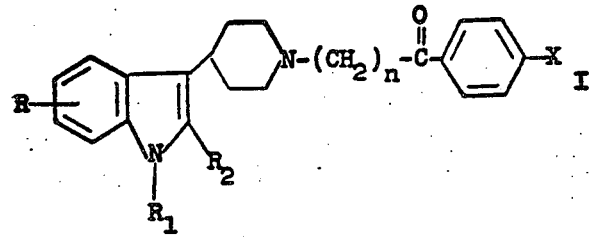

wherein R is selected from the group consisting of hydrogen and alkoxy of 1 to 5 carbon atoms, $R_1$ and $R_2$ are individually selected from the group consisting of hydrogen and alkyl of 1 to 5 carbon atoms, $n$ is 2 or 3 and X is selected from the group consisting of hydrogen, fluorine, chlorine and bromine and their non-toxic, pharmaceutically acceptable acid addition salts having central nervous system depressant activity.

12 Claims, No Drawings

OMEGA-[4-(3''-INDOLYL)-PIPERIDINO]-ALKYL-ARYLKETONES AS NEVROLEPTICS

PRIOR APPLICATION

This application is a division of copending, commonly assigned application Ser. No. 380,407 filed July 18, 1973, now U.S. Pat. No. 3,850,938.

STATE OF THE ART

British patent No. 925,429 describes several 4-(3-indolyl alkylene)-piperidines and U.S. Pat. No. 3,445,472 describes various 4-[2-(3-indolyl)-ethyl]-piperidines but the compounds of formula I have not been described in the literature.

OBJECTS OF THE INVENTION

It is an object of the invention to provide the novel compounds of formula I and their non-toxic, pharmaceutically acceptable acid addition salts.

It is a further object of the invention to provide a novel process for the preparation of compounds of formula I.

It is another object of the invention to provide novel neuroleptic compositions and to a method of treating warmblooded animals with neurovegatative unbalance, behavior troubles or character troubles.

These and other objects and advantages of the invention will become obvious from the following detailed description.

THE INVENTION

The novel compounds of the invention are selected from the group consisting of compounds of the formula

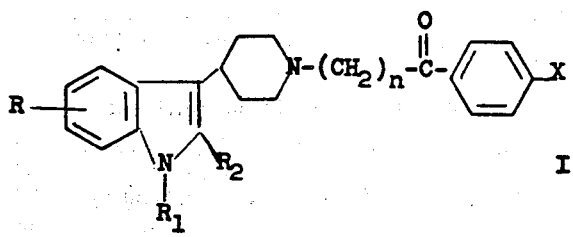

wherein R is selected from the group consisting of hydrogen and alkoxy of 1 to 5 carbon atoms, $R_1$ and $R_2$ are individually selected from the group consisting of hydrogen and alkyl of 1 to 5 carbon atoms, $n$ is 2 or 3 and X is selected from the group consisting of hydrogen, fluorine, chlorine and bromine and their non-toxic, pharmaceutically acceptable acid addition salts. Preferably, R is hydrogen or methoxy.

Among the preferred compounds are p-fluoro-ω-[4'-(3''-indolyl)-piperidino]-butyrophenone, p-fluoro-ω-[4'-(1''-methyl-3''-indolyl)-piperidino]-butyrophenone, p-fluoro-ω-[4'-(6''-methoxy-3''-indolyl)-piperidino]-butyrophenone, p-fluoro-ω-[4'-(5''-methoxy-3''-indolyl)-piperidino]-butyrophenone, p-fluoro-ω-[4'-(2''-methyl-6''-methoxy-3''-indolyl)-piperidino]-butyrophenone and ω-[4'-(3''-indolyl)-piperidino]-butyrophenone and their non-toxic, pharmaceutically acceptable acid addition salts.

Examples of suitable acids for the preparation of the acid addition salts are organic acids such as acetic acid, maleic acid, fumaric acid, succinic acid, tartaric acid, citric acid, oxalic acid, alkane sulfonic acids and aryl sulfonic acids and mineral acids such as hydrochloric acid, hydrobromic acid, hydroiodic acid, nitric acid, sulfuric acid and phosphoric acid.

The novel process of the invention for the preparation of compounds of formula I comprises reacting a compound of the formula

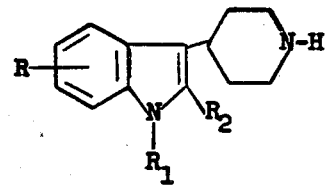

wherein R, $R_1$ and $R_2$ have the above definitions with a compound of the formula

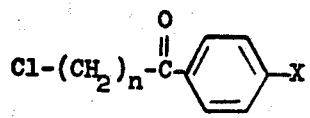

wherein $n$ and X have the above definition to form the corresponding compound of formula I which can then be reacted, if desired, with an organic or mineral acid to form the corresponding acid addition salt.

In a preferred mode of the process of the invention, a mixture of the product of formula II and the product of formula III is refluxed for 10 to 96 hours in an organic solvent such as methyl isobutyl ketone in the presence of an alkaline agent such as sodium carbonate and after completion of the reaction, the alkaline agent and the solvent are eliminated to obtain the product of formula I. The latter products are basic in nature and when treated with substantially stoichiometric amounts of an organic or mineral acid, the corresponding acid addition salts can be recovered.

The starting materials of formula II can be prepared by reacting benzyl bromide with a compound of the formula

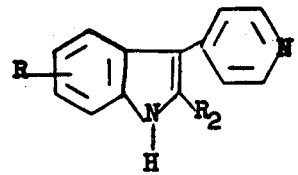

wherein R and $R_2$ have the above definition to form a compound of the formula

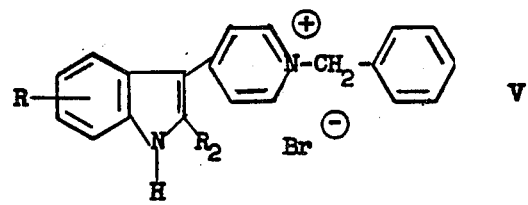

reacting the latter with sodium borohydride to obtain a compound of the formula

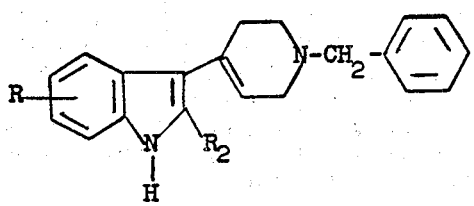

VI and the latter product may be reduced with hydrogen in the presence of a catalyst based on palladium to obtain a product of formula II wherein $R_1$ is hydrogen or may be reacted with an alkyl halide of the formula Hal-$R_1$ where Hal is a halogen and $R_1$ is lower alkyl of 1 to 5 carbon atoms in the presence of sodium hydride to obtain a product of the formula

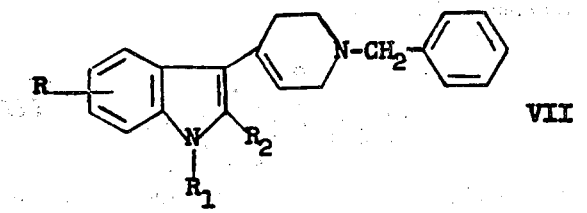

VII wherein $R_1$ is alkyl of 1 to 5 carbon atoms and R and $R_2$ have the above definition and the latter is reduced with hydrogen in the presence of a palladium based catalyst to obtain the corresponding compound of formula II.

The novel neuroleptic compositions of the invention are comprised of an effective amount of at least one compound of formula I and or their non-toxic, pharmaceutically acceptable acid addition salts and a pharmaceutical carrier. The compositions may be solids or liquids in the form of tablets, dragees, gelules, granules, suppositories and injectable solution or suspensions in single or multiple dose flacons.

Examples of suitable carriers or excipients are talc, gum arabic, lactose, amidon, magnesium stearate, cacao butter, aqueous or non-aqueous vehicles, fatty bodies of animal or vegetable origin, paraffinic derivatives, glycols, conservatives and/or diverse wetting, dispersing or emulsifying agents.

The said compositions have a remarkable depressant activity on the central nervous system of warm-blooded animals and are very useful substances in therapy for the treatment of neurovegatative unbalance, behavior troubles or character troubles.

The novel method of the invention for depressing the central nervous system of warm-blooded animals comprises administering to warm-blooded animals an effective amount of at least one compound of formula I and their non-toxic, pharmaceutically acceptable acid addition salts. The said products may be administered orally, rectally or parenterally and the usual useful daily dose is 0.1 to 10 mg/kg depending upon the product and the method of administration.

In the following examples there are described several preferred embodiments to illustrate the invention. However, it should be understood that the invention is not intended to be limited to the specific embodiments.

EXAMPLE 1 p-fluoro-ω-[4'-(3''-indolyl)-piperidino]-butyrophenone hydrochloride

A few crystals of potassium iodide were added to a mixture of 15 g of 3-(4'-piperidyl)-indole, 22 g of ω-chloro-p-fluoro-butyrophenone and 17.2 g of sodium carbonate in 670 ml of methyl isobutyl ketone and the resulting mixture was refluxed for 48 hours. The mixture was filtered hot and the ketone was distilled from filtrate under reduced pressure. The residue was taken up in ethanolic hydrochloric acid and the mixture was evaporated to dryness under reduced pressure. The product was crystallized from methanol to obtain 14.1 g of p-fluoro-ω-[4'-(3''-indolyl)-piperidino]-butyrophenone hydrochloride melting at 218°–219°C.

Analysis: $C_{23}H_{26}ClFN_2O$; molecular weight = 400.9

| Calculated: | %C 68.90 | %H 6.54 |
|---|---|---|
| Found: | 68.65 | 6.87 |

EXAMPLE 2 p-fluoro-ω-[4'-(1''-methyl-3''-indolyl)-piperidino]-butyrophenone hydrochloride

STEP A:
3-(1'-benzyl-1',2',3',6'-tetrahydro-4'-pyridyl)-1 methyl-indole

A solution of 43 g of 3-(1'-benzyl-1',2',3',6'-tetrahydro-4'-pyridyl)-indole in 225 ml of dimethylformamide was added dropwise in the absence of humidity to 7.5 g of 50% sodium hydride in oil, in 75 ml of dimethylformamide and the mixture was heated to 50°C for a half hour. The mixture was then cooled to 0° to 5°C and 10.4 ml of methyl iodide were added thereto. The mixture was then heated at 40°C for 3 hours and cooled and 200 ml of water was added progressively. The precipitate formed was recovered by vacuum filtration, was dried under reduced pressure and crystallized from acetone to obtain 34.5 g of 3-(1'-benzyl-1',2',3',6'-tetrahydro-4'-pyridyl)-1-methyl-indole melting at 103°–104°C.

STEP B: 1-methyl-3-(4'piperidyl-indole

Hydrogen was added with stirring to a mixture of 30.2 g of 3-(1'-benzyl-1',2',3',6'-tetrahydro-4'-pyridyl-1-methyl-indole in 300 ml of acetic acid and 3 g of 10% palladium on carbon at normal pressure at 50°C. After the theoretical quantity of hydrogen had been absorbed, the catalyst was filtered off. The acetic acid was evaporated from the filtrate under reduced pressure and the residue was taken up in water. The solution was made alkaline with a sodium hydroxide solution and was extracted with methylene chloride. The extracts were dried over sodium sulfate and the solvent was evaporated under reduced pressure to obtain after crystallization 14.5 g of 1-methyl-3-(4'-piperidyl)-indole melting at 78°–79°C.

STEP C:
p-fluoro-ω-[4'-(1''-methyl-3''-indolyl)-piperidino]-butyrophenone hydrochloride A few crystals of potassium iodide were added to a mixture of 9.80 g of ω-chloro-p-fluoro-butyrophenone, 9.5 g of 1-methyl-3-(4'-piperidyl)-indole and 11 g of sodium carbonate in 500 ml of methyl isobutyl ketone and the mixture was refluxed for 24 hours. Another 9.80 g of ω-chloro-p-fluoro-butyrophenone were added thereto and the mixture was refluxed for another 48 hours. After cooling, the organic phase was washed with water and after drying over sodium sulfate, the methyl isobutyl ketone was evporated. The resulting oil was taken up in ether and the ether solution was filtered. The filtrate was added to 12 ml of 4 N hydrochloric acid in ethyl ether and the precipitate formed was recovered by vacuum filtration, was washed with ether and crystallized from methanol to obtain after drying 8.7 g of p-fluoro-ω-[4'(1''-methyl-3''-indolyl)-piperidino]-butyrophenone hydrochloride melting at 260°C.

Analysis: $C_{24}H_{28}ClFN_2O$; molecular weight = 414.9

| Calculated: | %C 69.47 | %H 6.80 | %N 6.75 | %Cl 8.54 |
|---|---|---|---|---|
| Found: | 69.38 | 6.91 | 6.79 | 8.59 |

EXAMPLE 3 p-fluoro-ω-[4'-(6''-methoxy-3''-indolyl)-piperidino]-butyrophenone hydrochloride

STEP A: 6-methoxy-3-(4'-pyridyl)-indole 158 ml of benzoyl chloride were added dropwise to a mixture of 100 g of 6-methoxy-indole in 500 ml of pyridine cooled to −10°C and the mixture was then stirred in the dark at room temperature for 3 days. The pyridine was evaporated under reduced pressure and the residue was washed with ether and was then taken up in a liter of methanol. The solution was made alkaline with a sodium hydroxide solution and the methanol was evaporated under reduced pressure. The mixture was acidified with hydrochloric acid and was washed with methylene chloride. The mixture was made alkaline with sodium hydroxide and was extracted with chloroform. The organic phase was dried over sodium sulfate and was evaporated under reduced pressure. The residue was crystallized from acetonitrile to obtain 23.3 g of 6-methoxy-3-(4'-pyridyl)-indole melting at 187°–188°C.

Analysis: $C_{14}H_{12}N_2O$; molecular weight = 224.3

| Calculated: | %C 74.99 | %H 5.38 | %N 12.49 |
|---|---|---|---|
| Found: | 75.04 | 5.56 | 12.55 |

STEP B:
1-benzyl-4-(6'-methoxy-3'-indolyl)-pyridinium bromide

A mixture of 3.1 g of 6-methoxy-3-(4'-pyridyl)-indole and 2.56 g of benzyl bromide in 30 ml of ethyl acetate was refluxed for 4 hours and after cooling, was vacuum filtered to recover the precipitate formed. The latter was washed with ethyl acetate and dried to obtain 5.1 g of 1-benzyl-4-(6'-methoxy-3'-indolyl)-pyridinium bromide melting at 202°C.

Analysis: $C_{21}H_{19}BrN_2O$; molecular weight = 395.3

| Calculated: | %C 63.80 | %H 4.84 | %N 7.09 |
|---|---|---|---|
| Found: | 63.57 | 4.91 | 6.93 |

STEP C:
3-(1'-benzyl-1',2',3',6'-tetrahydro-4'-pyridyl)-6-methoxy-indole 4.6 g of 1-benzyl-4-(6'-methoxy-3'-indolyl)-pyridinium bromide were added at 40°C to 45 ml of methanol and 26 ml of water and the mixture was cooled to 25°C. 0.95 g of sodium borohydride were added thereto while keeping the temperature below 30° to 35°C and after stirring for 2 hours at room temperature, the mixture was added to water. The precipitate formed was recovered by vacuum filtration, was washed with water, then with methanol and dried to obtain 3.2 g of 3-(1'-benzyl-1',2',3',6'-tetrahydro-4'-pyridyl)-6-methoxy-indole melting at 196°C.

Analysis: $C_{21}H_{22}N_2O$; molecular weight = 318.40

| Calculated: | %C 79.21 | %H 6.96 | %N 8.80 |
|---|---|---|---|
| Found: | 78.9 | 6.8 | 8.7 |

STEP D: 6-methoxy-3-(4'-piperidyl)-indole

Hydrogen was added to a mixture of 21 g of 3-(1'-benzyl-1',2',3',6'-tetrahydro-4'-pyridyl)-6-methoxy-indole and 2 g of 10% palladium on carbon in 300 ml of methanol while heating at 55°C and the theoretical amount of hydrogen was absorbed in 36 hours. The catalyst was filtered off and the ethanol was evaporated from the filtrate. The oil residue was crystallized from ethyl acetate and then acetone to obtain 8.1 g of 6-methoxy-3-(4'-piperidyl)-indole which was used as is for the next step.

STEP E:
p-fluoro-ω-[4'-(6''methoxy-3''-indolyl)-piperidino]-butyrophenone hydrochloride A few crystals of potassium iodide were added to a mixture of 8 g of 6-methoxy-3-(4'-piperidyl)-indole, 10.4 g of ω-chloro-p-fluoro-butyrophenone and 8 g of sodium carbonate in 320 ml of methyl isobutyl ketone and the mixture was refluxed for 48 hours. The organic phase was then washed with water, dried over calcium chloride and the solvent was evaporated. The residue was taken up in ether and dilute hydrochloric acid was added thereto. The precipitate formed was recovered, dried and then dissolved in a boiling ethanolacetonitrile mixture and after the addition of ethanolic hydrochloric acid, the mixture was evaporated to dryness. The product was crystallized from a methanol-ether mixture to obtain 4.3 g of p-fluoro-ω-[4'-(6''-methoxy 3''-indolyl)-piperidino]-butyrophenone hydrochloride melting at 240°–243°C.

Analysis: $C_{24}H_{28}ClFN_2O_2$; molecular weight = 431

| Calculated: | %C 66.89 | %H 6.55 | %N 6.50 | %Cl 8.23 |
|---|---|---|---|---|
| Found: | 66.45 | 6.86 | 6.41 | 8.22 |

EXAMPLE 4 p-fluoro-ω-[4'-(5''-methoxy-3''-indolyl)-piperidino]-butyrophenone hydrochloride

STEP A:
1-benzyl-4-(5'-methoxy-3'-indolyl)-pyridinium bromide

A mixture of 11 g of 5-methoxy-3-(4'-pyridyl)-indole [prepared by Example 1 of French patent 1,587,692], 9.5 g of benzyl bromide and 120 ml of ethyl acetate was refluxed for 4 hours and the mixture was cooled and filtered. The precipitate was washed with ethyl acetate and dried under reduced pressure to obtain 17.5 g of 1-benzyl-4-(5'-methoxy-3'-indolyl)-pyridinium bromide melting at 254°C. The product was used as is for the next step.

STEP B:
3-(1'-benzyl-1',2',3',6'-tetrahydro-4'-pyridyl)-5-methoxy-indole 3.5 g of sodium borohydride were added in small portions to a mixture of 17.5 g of 1-benzyl-4-(5'-methoxy-3'-indolyl-pyridinium bromide in 150 ml of methanol and 65 ml of water at 40°C and after stirring the mixture for 24 hours at room temperature, 150 ml of water were added thereto. The precipitate formed was recovered by vacuum filtration, was washed with water, dried and crystallized from methanol to obtain 13 g of 3-(1'-benzyl-1',2',3',6'-tetrahydro-4'-pyridyl)-5-methoxy-indole melting at 168°C.

Analysis: $C_{21}H_{22}N_2O$; molecular weight = 318.30

| | %C | %H | %N |
|---|---|---|---|
| Calculated: | 79.21 | 6.96 | 8.80 |
| Found: | 78.9 | 6.9 | 8.7 |

STEP C: 5-methoxy-3-(4'-piperidyl)-indole

A mixture of 12.5 g of 3-(1'-benzyl-1',2',3',6'-tetrahydro-4'-pyridyl)-5-methoxy-indole and 3 g of 10% palladized charcoal in 300 ml of ethanol was heated to 50°C and 1770 ml of hydrogen were absorbed by the mixture in 7 hours. At the end of the reaction, the catalyst was filtered off and the filtrate was evaporated to dryness under reduced pressure to obtain 8.3 g of 5-methoxy-3-(4'-piperidyl)-indole melting at 170°C.

Analysis: $C_{14}H_{18}N_2O$; molecular weight = 230.31

| | %C | %H | %N |
|---|---|---|---|
| Calculated: | 73.01 | 7.88 | 12.17 |
| Found: | 73.0 | 7.6 | 12.1 |

STEP D:
p-fluoro-ω-[4'-(5''-methoxy-3''-indolyl)-piperidino]-butyrophenone hydrochloride A few crystals of potassium iodide were added to a mixture of 7.9 g of 5-methoxy-3-(4'-piperidyl)-indole 10.4 g d'ω-chloro-p-fluorobutyrophenone, and 7.9 g of sodium carbonate in 250 ml of methyl isobutyl ketone and the mixture was refluxed for 48 hours. After cooling, 150 ml of water were added thereto and the organic phase was decanted off, dried over calcium chloride and evaporated to dryness under reduced pressure. The residue was taken up in 400 ml of ether and the solution was filtered. 5 N hydrochloric acid in ether was added dropwise and the precipitate formed was recovered by vacuum filtration, was washed with ether and dried to obtain 15 g of product which was cristallized from absolute ethanol. After 2 successive crystallizations from absolute ethanol, 5.0 g of p-fluoro-ω-[4'-(5''-methoxy-3''-indolyl) piperidino]-butyrophenone hydrochloride melting at 220°C are obtained.

Analysis: $C_{24}H_{28}FClN_2O_2$; molecular weight = 430.96

| | %C | %H | %N | %F |
|---|---|---|---|---|
| Calculated: | 66.89 | 6.55 | 6.50 | 4.41 |
| Found: | 67.1 | 6.3 | 6.3 | 4.6 |

EXAMPLE 5
p-fluoro-ω-[4'-(2''-methyl-6''-methoxy-3''-indolyl)-piperidino]butyrophenone

STEP A: 2-methyl-6-methoxy-3-(4'-pyridyl)-indole 87 g of benzoyl chloride were added dropwise to a mixture of 50 g of 2-methyl-6-methoxy-indole in 230 ml of pyridine cooled to −40°C and the mixture was stirred for 3 days in the dark at room temperature. The pyridine was evaporated under reduced pressure and the residue was washed with aqueous sodium hydroxide solution. The water was evaporated and the product was dissolved in 500 ml of boiling methanol, then 200 ml of sodium hydroxide solution with stirring and then twice 200 ml of water were added thereto. The mixture was stirred for 2 hours and allowed to stand overnight after which the methanol was evaporated under reduced pressure. The aqueous phase was extracted with chloroform and the organic phase was dried over sodium sulfate and evaporated under reduced pressure to obtain 100 g of product. The latter was purified by chromatography over alumina and benzene was the eluant which was evaporated to obtain 34 g of product which was crystallized from acetonitrile to obtain 19.5 g of 2-methyl-6-methoxy-3-(4'-pyridyl)-indole melting at 196°–198°C.

Analysis: $C_{15}H_{14}N_2O$; molecular weight = 238.29

| | %C | %H | %N |
|---|---|---|---|
| Calculated: | 75.60 | 5.92 | 11.76 |
| Found: | 75.52 | 6.13 | 11.91 |

STEP B:
1-benzyl-4-(6'-methoxy-2'-methyl-3'-indolyl)-pyridinium bromide

A mixture of 3.4 g of 2-methyl-6-methoxy-3-(4'-pyridyl)indole and 2.65 g of benzyl bromide in 30 ml of ethyl acetate was refluxed for 4 hours and then was cooled. The crystals formed were recovered by vacuum filtration and were washed with ethyl acetate and dried to obtain 5.7 g of 1-benzyl-4-(6'-methoxy-2'-methyl-3'-indolyl)-pyridinium bromide melting at 244°–246°C.

Analysis: $C_{22}H_{21}BrN_2O$; molecular weight = 409.34

| | %C | %H | %N |
|---|---|---|---|
| Calculated: | 64.55 | 5.17 | 6.84 |
| Found: | 64.36 | 5.33 | 6.75 |

STEP C:
3-(1'-benzyl-1',2',3',6'-tetrahydro-4'-pyridyl)-6-methoxy-2-methyl-indole 20.1 g of 1-benzyl-4-(6'-methoxy-2'-methyl-3'-indolyl)pyridinium bromide were added at 35°–40°C to 165 ml of methanol and 70 ml of water and after cooling to 25°C, 4 g of sodium borohydride were added thereto in small amounts while keeping the temperature below 30°–35°C. The mixture was stirred for 2 hours at room temperature and water was then added. The crystals formed were recovered by vacuum filtration, were washed with water and dried under reduced pressure to obtain 15.4 g of 3-(1'-benzyl-1',2',3',6'-tetrahydro-4'-pyridyl)-6-methoxy-2-methyl-indole melting at 142°–143°C.

Analysis: $C_{22}H_{24}N_2O$; molecular weight = 332.45

| | %C | %H | %N |
|---|---|---|---|
| Calculated: | 79.48 | 7.28 | 8.43 |
| Found: | 79.40 | 7.44 | 8.35 |

STEP D: 6-methoxy-2-methyl-3-(4'-piperidyl)-indole

A mixture of 24 g of 3-(1'-benzyl-1',2',3',6'-tetrahydro-4'-pyridyl)-6-methoxy-2-methoxy-indole and 4 g of 10% palladized carbon in 300 ml of absolute ethanol was heated to 50°C and hydrogen was introduced for 12 hours during which 2,450 ml of hydrogen were absorbed. The catalyst was filtered off and another 3 g of 10% palladized carbon were added. Hydrogenation was continued for 3 ½ hours during which 3,250 ml of hydrogen were absorbed. The catalyst was filtered off and ethanol was evaporated from the filtrate under reduced pressure to obtain 16.6 g of 6-methoxy-2-methyl-3-(4'-piperidyl)-indole melting at 166°C.

Analysis: $C_{15}H_{20}N_2O$; molecular weight = 244.34

| | %C 73.73 | %H 8.25 | %N 11.47 |
|---|---|---|---|
| Calculated: | 73.6 | 8.3 | 11.5 |
| Found: | | | |

STEP E:
p-fluoro-ω-[4'-(2''-methyl-6''-methoxy-3''-indolyl)-piperidino]-butyrophenone A few crystals of potassium iodide were added to a mixture of 16 g of 6-methoxy-2-methyl-3-(4'-piperidyl)-indole, 20 g of ω-chloro-p-fluorobutyrophenone and 15 g of sodium carbonate in 500 ml of methyl isobutyl ketone and the mixture was refluxed for 48 hours and then cooled. 200 ml of water were added thereto and the organic phase was decanted off, dried over calcium chloride and evaporated to dryness under reduced pressure to obtain 25.6g of product. The product was crystallized from acetonitrile and dried to obtain 13.8 g of p-fluoro-ω-[4'-(2''-methyl-6''-methoxy-3''-indolyl)-piperidino]-butyrophenone melting at 162°C.

Analysis: $C_{25}H_{29}FN_2O_2$; molecular weight = 408.52

| | %C 73.50 | %H 7.15 | %F 4.65 | %N 6.86 |
|---|---|---|---|---|
| Calculated: | 73.4 | 7.4 | 4.5 | 7.1 |
| Found: | | | | |

EXAMPLE 6
p-bromo-ω-[4'-(3''-indolyl)-piperidino]-butyrophenone hydrochloride A few crystals of potassium iodide were added to a mixture of 5 g of 3-(4'-piperidyl)-indole, 9.2 g of p-bromo-ω-chloro-butyrophenone and 10.6 g of sodium carbonate in 350 ml of methyl isobutyl ketone and the mixture was refluxed for 48 hours and then was cooled. Water was added thereto and the organic phase was decanted off, dried over sodium sulfate and evaporated to dryness under reduced pressure to obtain 6.8 g of an oily product which was dissolved in ether. The solution was filtered, acidified with ethanolic hydrochloric acid and was vacuum filtered. The precipitate was dried to obtain 3.4 g of product which was crystallized from absolute ethanol to obtain 2 g of p-bromo-ω-[4'-(3''-indolyl)piperidino]-butyrophenone hydrochloride melting at 208°–210°C.

Analysis: $C_{23}H_{26}BrClN_2O$; molecular weight = 461.85

| | %C 59.81 | %H 5.67 | %Br 17.30 | %Cl 7.68 |
|---|---|---|---|---|
| Calculated: | 60.1 | 5.6 | 17.5 | 7.9 |
| Found: | | | | |

EXAMPLE 7
ω-[4'-(3'-indolyl)-piperidino]-butyrophenone hydrochloride

A few crystals of potassium iodide were added to a mixture of 5 g of 3-(4'-piperidyl)-indole, 6.4 g of ω-chlorobutyrophenone and 10.6g of sodium carbonate in 350 ml of methyl isobutyl ketone and the mixture was refluxed for 48 hours and then cooled. Water was added and the organic phase was recovered by decanting, was dried over sodium sulfate and evaporated to dryness under reduced pressure to obtain 9.5 g of an oily product which was dissolved in ether. The ether solution was filtered, acidified with ethanolic hydrochloric acid and was vacuum filtered. The precipitate was dried and twice successively crystallized from methanol to obtain 2.5g of ω-[4'(3''-indolyl)-piperidino]-butyrophenone hydrochloride melting at 230°–232°C.

Analysis: $C_{23}H_{27}ClN_2O$; molecular weight = 382.94

| | %C 72.14 | %H 7.11 | %N 7.31 | %Cl 9.26 |
|---|---|---|---|---|
| Calculated: | 71.8 | 7.2 | 7.2 | 9.4 |
| Found: | | | | |

EXAMPLE 8
p-fluoro-γ-[4'-(3''-indolyl)-piperidino]-propiophenone hydrochloride A few crystals of potassium iodide were added to a mixture of 6 g of 3-(4'-piperidyl)-indole, 8.4 g of β-chloro-p-fluoro-propiophenone and 12.7 g of sodium carbonate in 420 ml of methyl isobutyl ketone and the mixture was refluxed for 48 hours and then cooled. Water was added thereto and the organic phase was recovered by decanting, was dried over sodium sulfate and evaporated to dryness under reduced pressure to obtain 14.5 g of oily product which was dissolved in ether. The solution was filtered, acidified with ethanolic hydrochloric acid and vacuum filtered. The precipitate was dried and crystallized from methanol to obtain 3.3 g of p-fluoro-γ-[4'-(3''-indolyl)-piperidino]-propiophenone hydrochloride melting at 200°C.

Analysis: $C_{22}H_{24}ClFN_2O$; molecular weight = 386.90

| | %C 68.29 | %H 6.25 | %F 4.91 | %Cl 9.16 | %N 7.24 |
|---|---|---|---|---|---|
| Calculated: | 68.0 | 6.6 | 5.0 | 9.1 | 7.4 |
| Found: | | | | | |

EXAMPLE 9

Tablets were prepared containing 25 mg of p-fluoro-ω-[4'-(3''-indolyl)-piperidino]-butyrophenone hydrochloride and an excipient of lactose, amidon, talc and magnessium stearate. Similar tablets were prepared containing 25 mg of p-fluoro-ω-[4'-(6''-methoxy-3''-indolyl)-piperidino]-butyrophenone hydrochloride.

PHARMACOLOGICAL STUDY

A. Neuroleptic Activity

The neuroleptic activity of the compounds of Examples 1 to 8 were determined in the following 4 tests and the results are reported in Table I:

a. The traction test which consists of suspending a mouse by his front paws from a metal wire stretched horizontally. In a time less than 5 seconds, the normal animal effected recovering by managing to bring one of the rear paws to the wire. The test was run 25 minutes after intraperitoneal administration of the test product to determine the $DE_{50}$ dose at which 50% of the animals effected recovering in less than 5 seconds.

b. The chimney test which consists of placing a mouse in the extreme end of a glass tube 30 cm long and with a diameter adapted to the size of the animal. This tube is straightened vertically in a rapid motion and the animal with its head down mounts normally the length of the tube in less than 30 seconds. The test was effected 25 minutes after intraperitoneal administration of the test compounds to determine the $DE_{50}$ dose which is the dose at which 50% of the animals effected a mounting in less than 30 seconds.

c. The cataleptic activity test using the technique of Boissier et al [Therapie, Vol. 18 (1963), p. 1257–1277] with a young rat having slightly twisted homolaterally paws and noting the intensity of catalepsy. The $DE_{50}$ dose is that dose provoking catalepsy in 50% of the animals after administration of the product.

d. The anti-emetic activity test which is determined on dogs vis-a-vis a subcutaneous injection of 0.1 mg/kg of apomorphine hydrochloride to determine the $DE_{50}$ dose which is that dose which reduces 50% of the number of vomitings provoked by the injection of apomorphine hydrochloride.

TABLE 1

| Product of Example | $DE_{50}$ in mg/Kg (I.P.) | | | |
|---|---|---|---|---|
| | Traction Test | Chimney Test | Test of Cataleptic Activity | Test of Anti-emetic Activity |
| 1 | 2.2 | 1.6 | 8.5 | 0.02 |
| 2 | 5.2 | 4.5 | 12 | 0.2 |
| 3 | 1.2 | 0.9 | 2 | 0.01 |
| 4 | 1 | 0.2 | 6 | <0.3 |
| 5 | 3.8 | 0.3 | 3.5 | 0.0045 |
| 7 | 7 | 4 | 11 | 0.06 |
| 8 | 2.5 | 2.7 | | |

Table I shows that the compounds of the invention have very interesting neuroleptic activity, particularly the compounds of Examples 1,3,4 and 5.

B. Acute Toxicity

The different products were tested for the dose which would kill 50% of mice when administered intraperitoneally ($DL_{50}$). The mortality was recorded 48 hours after administration of the products and the results are reported in Table II.

TABLE 2

| Product of Example | $DL_{50}$ in mg/Kg I.P. |
|---|---|
| 1 | 100 |
| 2 | 185 |
| 3 | 190 |
| 4 | 300 |
| 5 | 600 |
| 6 | 300 |
| 7 | 300 |
| 8 | 600 |

Various modifications of the products and processes of the invention may be made without departing from the spirit or scope thereof and it is to be understood that the invention is to be limited only as defined in the appended claims.

We claim:

1. A novel neuroleptic composition comprising an effective amount of a compound of the formula

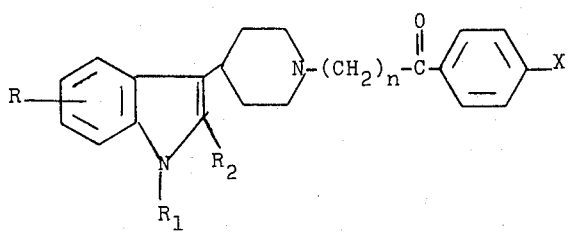

wherein R is selected from the group consisting of hydrogen and alkoxy of 1 to 5 carbon atoms, $R_1$ and $R_2$ are individually selected from the group consisting of hydrogen and alkyl of 1 to 5 carbon atoms, n is 2 or 3 and X is selected from the group consisting of hydrogen, fluorine, chlorine and bromine or a non-toxic, pharmaceutically acceptable acid addition salt thereof and a pharmaceutical carrier.

2. A composition of claim 1 wherein R is selected from the group consisting of hydrogen and methoxy.

3. A method of depressing the central nervous system of a warm-blooded animal comprising administering to a warm-blooded animal an amount of a compound of the formula

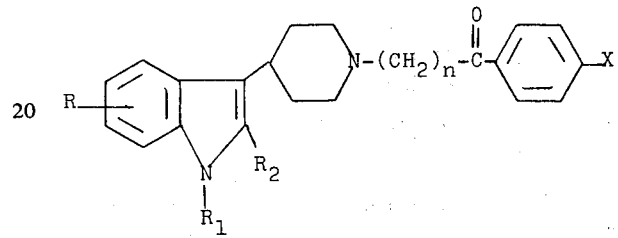

wherein R is selected from the group consisting of hydrogen and alkoxy of 1 to 5 carbon atoms, $R_1$ and $R_2$ are individually selected from the group consisting of hydrogen and alkyl of 1 to 5 carbon atoms, n is 2 or 3 and X is selected from the group consisting of hydrogen, fluorine, chlorine and bromine or a non-toxic, pharmaceutically acceptable acid addition salt thereof sufficient to depress the central nervous system.

4. The method of claim 3 wherein R is selected from the group consisting of hydrogen and methoxy.

5. The method of claim 3 selected from the group consisting of p-fluoro-ω-[4'-(3''-indolyl)-piperidino]-butyrophene and its non-toxic, pharmaceutically acceptable acid addition salts.

6. The method of claim 3 selected from the group consisting of p-fluoro-ω-[4'-(1''-methyl-3''-indolyl)-piperidino]-butyrophenone and its non-toxic, pharmaceutically acceptable acid addition salts.

7. The method of claim 3 selected from the group consisting of p-fluoro-ω-[4'-(6''-methoxy-3''-indolyl)-piperidino]-butyrophenone and its non-toxic, pharmaceutically acceptable acid addition salts.

8. The method of claim 3 selected from the group consisting of p-fluoro-ω-[4'-(5''-methoxy-3''-indolyl)-piperidino]-butyrophenone and its non-toxic, pharmaceutically acceptable acid addition salts.

9. The method of claim 3 selected from the group consisting of p-fluoro-ω-[4'-(2''-methyl-6''-methoxy-3''-indolyl)-piperidino]-butyrophenone and its non-toxic, pharmaceutically acceptable acid addition salts.

10. The method of claim 3 selected from the group consistof ω-[4'-(3''-indolyl)-piperidino]-butyrophenone and its non-toxic, pharmaceutically acceptable acid addition salts.

11. The method of claim 3 selected from the group consisting of p-bromo-ω-[4'-(3''-indolyl)-piperidino]-butyrophenone and its non-toxic, pharmaceutically acceptable acid addition salts.

12. The method of claim 3 selected from the group consisting of p-fluoro-α-[4'-(3''-indolyl)-piperidino]-propiophenone and its non-toxic, pharmaceutically acceptable acid addition salts.

* * * * *

UNITED STATES PATENT OFFICE
CERTIFICATE OF CORRECTION

Patent No. 3,947,578　　　　　　　Dated　March 30, 1976

Inventor(s) PIERRE HENRI DERIBLE and JEAN-PAUL LAVAUX

It is certified that error appears in the above-identified patent and that said Letters Patent are hereby corrected as shown below:

| Col. | Line | Priority Date |
|---|---|---|
| [30] | | "July 29, 1972" should be --July 28, 1972-- |
| 4 | 30 | "0°" should be --0-- |
| 7 | 7 | "indolyl"- should be --indolyl)-- |
| 7 | 60 | --%Cl 8.23--omitted on right Col. |
| 7 | 61 | --8.5-- omitted on right Col. |
| 8 | 32 | "pyridyl)indole" should be --pyridyl)-indole-- |
| 8 | 47 | "indolyl)pyridinium" should be --indolyl)-pyridinium-- |
| 9 | 56 | "indolyl)piperidino" should be --indolyl)-piperidino-- |
| 10 | 11 | "ω-[4'(3"" shoul be --ω-[4'-(3"-- |

Signed and Sealed this

Fourteenth Day of September 1976

[SEAL]

Attest:

RUTH C. MASON
*Attesting Officer*

C. MARSHALL DANN
*Commissioner of Patents and Trademarks*